United States Patent [19]

Kawano et al.

[11] 4,305,929

[45] Dec. 15, 1981

[54] STICK-SHAPED COSMETIC MATERIAL

[75] Inventors: Junichi Kawano, Sakura; Toshiyuki Suzuki, Tokyo; Shigeo Inoue, Ichikai, all of Japan; Shizuo Hayashi, deceased, late of Sugito, Japan, by Horuko Hayashi, legal representative

[73] Assignee: Kao Soap Co., Ltd., Tokyo, Japan

[21] Appl. No.: 78,155

[22] Filed: Sep. 24, 1979

[30] Foreign Application Priority Data

Sep. 22, 1978 [JP] Japan ................. 53-116880

[51] Int. Cl.³ ................... A61K 7/021; A61K 7/027; A61K 7/031; A61K 7/032
[52] U.S. Cl. ............................ 424/63; 424/DIG. 5; 424/64
[58] Field of Search ................. 424/64, DIG. 5, 63; 536/116, 115

[56]  References Cited

U.S. PATENT DOCUMENTS

| 1,320,855 | 11/1919 | Henderson | 424/DIG. 5 |
|---|---|---|---|
| 2,422,633 | 6/1947 | Petersen | 536/119 |
| 2,450,079 | 9/1948 | Brown | 536/116 |
| 2,626,935 | 1/1953 | De Groote | 536/116 |
| 2,908,681 | 10/1959 | Anderson et al. | 536/116 |
| 3,102,114 | 8/1963 | Komori et al. | 536/116 |
| 4,032,702 | 6/1977 | James | 536/115 |

FOREIGN PATENT DOCUMENTS 51-14488 5/1976 Japan ................. 536/119

Primary Examiner—Dale R. Ore
Attorney, Agent, or Firm—Oblon, Fisher, Spivak, McClelland & Maier

[57]  ABSTRACT

A stick-shaped cosmetic material comprising a hydroxypropyl-etherified glycolipid ester represented by the general formula,

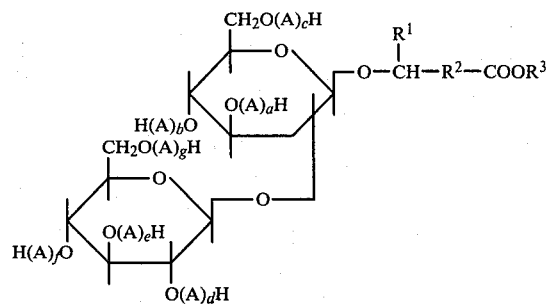

wherein $R^1$ represents a methyl group or a hydrogen atom, $R^2$ represents a saturated or unsaturated hydrocarbon group having carbon atoms of 11 to 15 when $R^1$ is a methyl group, or $R^2$ represents a saturated or unsaturated hydrocarbon group having carbon atoms of 12 to 16 when $R^1$ is a hydrogen atom, A represents the group

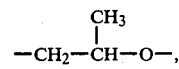

$R^3$ represents a saturated or unsaturated hydrocarbon group having carbon atoms of 1 to 20 or $-(A)_hH$, and a, b, c, d, e, f, g and h are integers, whose sum ranges from 1 to 60.

3 Claims, No Drawings

STICK-SHAPED COSMETIC MATERIAL

BACKGROUND OF THE INVENTION

1. Field of the Invention

This invention relates to stick-shaped cosmetic materials, more particularly to a novel stick-shaped cosmetic material comprising a hydroxypropyl-etherified glycolipid ester (hereinafter abbreviated as "POSL") represented by the following general formula (I);

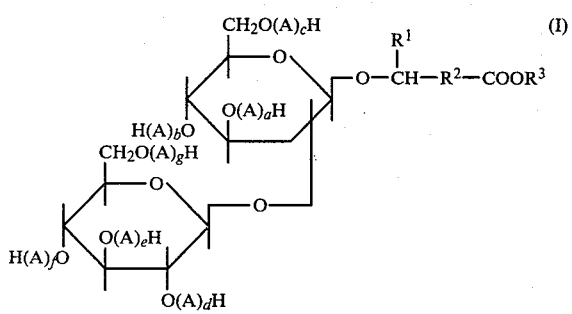

wherein $R^1$ represents a methyl group or a hydrogen atom, $R^2$ represents a saturated or unsaturated hydrocarbon group having carbon atoms of 11 to 15 when $R^1$ is a methyl group, or $R^2$ represents a saturated or unsaturated hydrocarbon group having carbon atoms of 12 to 16 when $R^1$ is a hydrogen atom, A represents the group of the formula

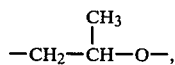

$R^3$ represents a saturated or unsaturated hydrocarbon group having carbon atoms of 1 to 20 or $-(A)_hH$, and a, b, c, d, e, f, g and h are integers, whose sum ranges from 1 to 60.

2. Description of the Prior Art

Known stick-shaped cosmetic materials have been usually produced by combining castor oil, plant oil, liquid paraffin, a synthetic ester oil, bees wax, carnauba wax, microcrystalline wax, and other fat and oil as major or adjunct components. However, the stick-shaped cosmetic materials thus formulated do not easily become homogeneous because of the combination of the various components. When stored for extended periods of time or subjected to changes such as temperatures and humidities, the stick-shaped cosmetic materials result in unbalanced miscibility of the components and induce sweating, bruming and variable compressive strengths. These drawbacks adversely affect the appearance and application feeling of the cosmetic material of the type described.

In order to overcome the above noted drawbacks, the present inventors have made a wide variety of studies, and as a result, have found that a stick-shaped cosmetic material of good and stable quality and performance can be produced by combination of POSL of the formula (I) in the composition.

Based on this finding, the present invention has been accomplished.

SUMMARY OF THE INVENTION

In accordance with the invention, there is provided a stick-shaped cosmetic material which comprises POSL represented by the formula (I) and which exhibits no sweating and bruming properties, nor does vary in compressive strength even if stored for a long period of time.

DETAILED DESCRIPTION OF THE PREFERRED EMBODIMENTS

POSL which is useful in the present invention is a novel compound which can be produced, for instance, by reacting glycolipid or a glycolipid ester represented by the general formula (II);

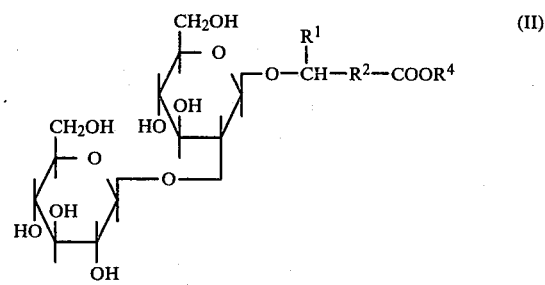

wherein $R^4$ represents a saturated or unsaturated hydrocarbon group having carbon atoms of 1 to 20 or a hydrogen atom, with propylene oxide in the presence of an alkali catalyst (Japanese Patent Application No. 24306/1978, U.S. Pat. No. 4,195,177, issued Mar. 25, 1980).

The properties of POSL which is useful in and typical of the present invention are shown below.

| $R^1$ | $R^2$ | $R^3$ | Addition mole number | Hydroxyl value | Acid value | Saponification value | Appearance |
|---|---|---|---|---|---|---|---|
| $CH_3$ | $C_{15}H_{28}$ | $CH_3$ | 5 | 420.3 | 0.2 | 61.3 | Viscous paste substance |
|  |  |  | 7 | 376.5 | 0.7 | 53.5 |  |
|  |  |  | 15 | 261.5 | 0.3 | 37.0 |  |
|  |  |  | 30 | 167.2 | 1.2 | 21.5 |  |
| $CH_3$ | $C_{15}H_{28}$ | $C_{12}H_{25}$ | 7 | 325.3 | 0.2 | 47.0 | Paste-like wax substance |
|  |  |  | 15 | 236.2 | 0.8 | 31.5 |  |
|  |  |  | 30 | 159.3 | 0.5 | 20.7 |  |
| $CH_3$ | $C_{15}H_{28}$ | $-(A)_hH$ | 5 | 492.0 | 0.7 | 60.5 | Viscous paste substance |
|  |  |  | 8 | 413.5 | 0.0 | 51.5 |  |
|  |  |  | 15 | 299.0 | 0.1 | 37.5 |  |
|  |  |  | 30 | 185.3 | 0.0 | 23.8 |  |

By the term stick-shaped cosmetic material is meant the so-called stick-shaped rouge, lip cream, stick-shaped eyeshadow or cosmetic pencil, which is produced by fusing the above fat, oil and wax, and mixing therewith a pigment, perfume and drug to make a homogeneous mixture, and subsequently pouring the resulting mixture into the mold, and cooling, solidifying and molding the same in its stick form.

The stick-shaped cosmetic material according to the present invention can be produced by any conventional method, with the exception that POSL is combined with the composition in an amount of 0.1 to 10% by weight, preferably 0.5 to 8% by weight, of the stick-shaped cosmetic material.

The invention will now be described in further detail with certain specific Examples, but the invention is not limited to these Examples. The Reference Example is illustrative of the preparation of POSL to be used in the invention.

Reference Example (i) To a mixture of 1500 g of glucose, 75 g of a yeast extract and 15 g of urea was added water to adjust the whole volume to 15 l, and the resulting mixture was sterilized and used as a fermentation liquid. To this fermentation liquid was inoculated Torpulopsis bombicola which had been cultured in the same culture medium as above at 30° C. for 48 hours. The fermentation was initiated under the following conditions: temperature, 20° C.; stirring, 300 rpm; and aeration, 0.33 VVM. The fermentation was conducted for 24 hours after inoculation of the microorganisms, and 150 g of beef tallow was added, followed by adding the same amount of beef tallow at intervals of 24 hours. The added beef tallow amounted to 900 g. After the final addition, the fermentation was continued for further 24 hours. The fermentation time totaled 168 hours. After the completion of the fermentation, a sophorolipid layer precipitating at the bottom of a fermentor was collected by decantation to give 1300 g of sophorolipid, which was a paste having a water content of about 50%.

(ii) 100 g of the thus obtained sophorolipid together with 2.5 g of polypropylene glycol having an average molecular weight of 200 was placed in a 200 ml round bottom flask equipped with a stirrer and a Liebig condenser. The mixture was evaporated with stirring in an oil bath (80° C.) under a reduced pressure of 250 mmHg to eliminate water. The distillation of water was completed in about 2 hours, and the water content at that time was found to be less 1%.

(iii) 150 g of methanol was added to the thus prepared polypropylene solution of sophorolipid, and to the resulting mixture was added 2.5 g of sulfuric acid. The mixture was reacted at 40° C.±2° C. for 90 minutes. The reaction was regarded as having reached completion when many spots of the raw material or sophorolipid converged on one spot corresponding to a glycolipid methyl ester by thin-layer chromatography on silica gel [developing solvent: chloroform-methanol-acetic acid (75:20:5)].

After the completion of the reaction, the mixture was made neutral with a given amount of potassium hydroxide and filtered. The filtrate was placed again in a round bottom flask equipped with a Liebig condenser, and methanol and methyl acetate were removed by distillation to obtain 48 g of a mixture containing 94% of a crude [(2'-O-β-D-glucopyranosyl-β-D-glucopyranosyl)oxy]alkanic acid and alkenic acid methyl ester as a brown paste and coexisting polypropylene glucose. This mixture was purified by column chromatography on silica gel to obtain a pure [(2'-O-β-D-glucopyranosyl-β-D-glucopyranosyl)oxy]alkanic acid and alkenic acid methyl ester.

IR (cm$^{-1}$): 1740 (<C=O ester), 1380~3200 (—OH sugar), 900~750 (glucopyranose ring).

NMR [δ(pyridine): 1.1~1.6 (—CH$_2$—CH$_2$—), 3.6 (—O—CH$_3$), 3.5~5.0 (sugar), 5.5 (—CH=CH— unsaturated fatty acid)

Oil-characteristics analysis: Acid value: 0, Hydroxy value: 615, Saponification value: 88, Ester value: 87.

(iv) In an autoclave were placed 100 g of the thus obtained mixture of the [(2'-O-β-D-glucopyranosyl-β-D-glucopyranosyl)oxy]alkanic acid and alkenic acid methyl ester with coexisting polypropylene glycol and 0.25 g of potassium hydroxide, and propylene oxide gas was bubbled into the mixture in an amount corresponding to a given addition mole number. The mixture was reacted at 100°-120° C. for 6 hours. After completion of the reaction, the mixture was neutralized with phosphoric acid and filtered under high pressure to obtain a crude product as a brown paste. This product was purified by chromatography on silica gel to obtain a pure polyoxypropylene-[(2'-O-β-D-glucopyranosyl-β-D-glucopyranosyl)oxy]alkanic acid and alkenic acid methyl ester as a pale yellow paste.

EXAMPLE 1

Commercial samples A to G, inventive samples H to Q having the following compositions (Tables 2 to 6) and produced by any known method, and usual samples R to T (total species of the stick-shaped cosmetic material were 20) were preserved at 10° C. for 4 hours and then at 40° C., 80% R.H. for 4 hours. Sweating was observed with the naked eye.

Bruming was also observed with the naked eye after the samples A to T were preserved at 40° C. for 8 hours and then at 5° C. for 24 hours.

The results obtained are shown in Table 1. From these results, it can be seen that the samples H to Q are very stable, with no sweating and bruming being observed.

TABLE 1

| Samples | Sample Marks | Sweating | Bruming |
|---|---|---|---|
| Commerical lip rouge | A | ++ | + |
|  | B | ++ | — |
|  | C | + | + |
| Commerical lip cream | D | +++ | ++ |
| Commerical stick-shaped eye-shadow | E | +++ | + |
|  | F | ++ | + |
|  | G | + | — |
| Present invention Lip rouge | H | — | — |
|  | I | — | — |
|  | J | — | — |
|  | K | — | — |
| Lip cream | L | — | — |
|  | M | — | — |
|  | N | — | — |
| Eye-shadow | O | — | — |
|  | P | — | — |
|  | Q | — | — |
| Lip rouge by the usual prescription | R | ++ | + |
|  | S | ++ | ++ |
| Eye-shadow by the usual prescription | T | + | + |

Evaluation Standards:
—: Nothing
+: Slight
++: Fair
+++: Severe

TABLE 2

(Stick-shaped lip rouge)

| Components | Sample Marks | | | |
|---|---|---|---|---|
| | H | I | J | K |
| Carnauba wax | 10 parts | 8 parts | 8 parts | 10 parts |
| Bees wax | 15 | 14 | 15 | 15 |
| Castor oil | 40 | 42 | 42 | 43 |
| Oleyl alcohol | 12 | 10 | 8 | 6 |
| Ceresine wax | 10 | 13 | 15 | 15 |
| Stearic acid | 1 | — | 1 | — |
| POSL (I) | — | — | 3 | 6 |
| POSL (II) | 3 | — | — | — |
| POSL (III) | — | 4 parts | — | — |
| Red iron oxide | 3 parts | 3 | 3 parts | 2 parts |
| Pigment (Red 202) | 2 | 2 | 2 | 2 |
| Titanium dioxide | 4 | 4 | 3 | 1 |

TABLE 3

(Stick-shaped lip cream)

| Components | Sample Marks | | |
|---|---|---|---|
| | L | M | N |
| Castor wax | 30 parts | 29 parts | 1 parts |
| Oleyl alcohol | 23 | 23 | 23 |
| Microcrystalline wax | 12 | 10 | 8 |
| Bees wax | 14 | 16 | 15 |
| Glycerine monostearate | 8 | 8 | 8 |
| POSL(I) | — | 4 | — |
| POSL(III) | 6 | — | — |
| POSL(IV) | — | — | 6 |
| Carnauba wax | 5 | 6 | 7 |
| Lanolin | 2 | 7 | 2 |

TABLE 4

(Stick-shaped eye-shadow)

| Components | Sample Marks | | |
|---|---|---|---|
| | O | P | Q |
| Castor wax | 20 parts | 20 parts | 20 parts |
| Oleyl alcohol | 25 | 27 | 22 |
| Squalane | 10 | 10 | 10 |
| Carnauba wax | 10 | 5 | 20 |
| Microcrystalline wax | 13 | 10 | 7 |
| Glycerine monostearate | 8 | 8 | 8 |
| POSL (I) | 4 parts | — | — |
| POSL (II) | — | 3 parts | 6 parts |
| Titanium oxide | 7 | 4 | 4 |
| Ultramarine | 3 | 3 | 3 |

TABLE 5

(Stick-shaped lip rouge by the usual prescription)

| Components | Sample Marks | |
|---|---|---|
| | R | S |
| Bees wax | 15 parts | 15 parts |
| Oxocerite | 10 | — |
| Carnauba wax | 5 | 10 |
| Ceresine wax | 4 | — |
| Lanolin | 5 | — |
| Lanolin absorption base | 14 | — |
| Isopropyl alcohol | 10 | — |
| Diethyl sebacate | 10 | — |
| Castor oil | 15 | 65 |
| Cetyl alcohol | — | 5 |
| Eosine | 2 | — |
| Bromic acid | — | 3 |
| Pigment | 10 | 7 |
| Antioxidant | optional | — |
| Perfume | optional | 0.3 |

TABLE 6

(Stick shaped eye-shadow by the usual prescription)

| Components | Sample Mark |
|---|---|
| | T |
| Ceresine | 26 parts |
| Hardened oil | 5 |
| Castor oil | 43 |
| Carnauba wax | 4 |
| Liquid paraffin | 6 |
| Titanium dioxide | 8 |
| Iron oxide (Red) | 4 |
| Iron oxide (Black) | 4 |

TABLE 7

(Explanation on POSL used in the preparation of the samples)

| | $R^1$ | $R^2$ | $R^3$ | Sum of a to h |
|---|---|---|---|---|
| POSL (I) | $CH_3$ | $C_{15}H_{28}$ | $CH_3$ | 7 |
| POSL (II) | $CH_3$ | $C_{15}H_{28}$ | $C_{12}H_{25}$ | 30 |
| POSL (III) | $CH_3$ | $C_{15}H_{28}$ | $CH_3$ $\vert$ $(CH_2\text{—}CH\text{—}O)_{\overline{n}}H$ | 5 |
| POSL (IV) | $CH_3$ | $C_{15}H_{28}$ | $CH_3$ $\vert$ $(CH_2\text{—}CH\text{—}O)_{\overline{n}}H$ | 15 |

EXAMPLE 2

Thirteen species extracted from the same samples A to T as used in Example 1 were cut crosswise, each having a thickness of 5 mm, and preserved at 5° C. and 30° C. for 12 hours. Any stresses were measured which were needed to cause destruction when compressed with a rheometer.

The results obtained are shown in Table 8. From these results, it can be seen that the commercially available samples and the samples by the usual prescription are large in their compressive strength ratios between 5° C. and 30° C., while the inventive samples are small in their compressive strength ratios between 5° C. and 30° C. This indicates that the inventive samples present only a small difference in application feeling under cold and warm conditions.

TABLE 8

| Sample Marks | Compressive strengths ($\times 10^6$ dyn/cm$^2$) | | Ratios of compressive strengths between 5° C. and 30° C. |
|---|---|---|---|
| | 5° C. | 30° C. | |
| A | 9.0 | 2.1 | 4.3 |
| B | 8.8 | 2.3 | 3.8 |
| D | 9.3 | 1.9 | 4.9 |
| E | 7.5 | 1.6 | 4.7 |
| H | 5.2 | 3.1 | 1.7 |
| I | 8.5 | 4.7 | 1.8 |
| K | 6.5 | 4.1 | 1.6 |
| L | 5.1 | 2.8 | 1.8 |
| N | 4.6 | 3.3 | 1.4 |
| O | 4.1 | 2.2 | 1.9 |
| R | 9.2 | 2.2 | 4.2 |
| S | 9.1 | 2.3 | 4.0 |
| T | 7.4 | 1.8 | 4.1 |

EXAMPLE 3

Five stick-shaped lip rouge species extracted from the samples A to H used in Example 1 were preserved at 5° C. and 40° C. for 48 hours. Each rouge was applied to the lips of five subjects who had stayed for 30 minutes in a chamber thermostated at 5° C. and 40° C.

The results obtained are shown in Table 9. From these results, it can be seen that the application feeling of the present samples is stable and excellent at 5° C. and 40° C.

TABLE 9

| | 5° C. | | | | | | 40° C. | | | | | |
|---|---|---|---|---|---|---|---|---|---|---|---|---|
| | 1 | 2 | 3 | 4 | 5 | Average | 1 | 2 | 3 | 4 | 5 | Average |
| B | +1 | +1 | +2 | +2 | +1 | 1.4 | −2 | −2 | −2 | −1 | −2 | −1.8 |
| C | +2 | +1 | +2 | +1 | +1 | 1.4 | −2 | −1 | −2 | −1 | −2 | −1.6 |
| I | +1 | 0 | 0 | +1 | 0 | 0.4 | −1 | 0 | −1 | 0 | −1 | −0.6 |
| K | 0 | +1 | 0 | +1 | +1 | 0.6 | 0 | −1 | 0 | −1 | 0 | −0.4 |
| R | +2 | +2 | +1 | +2 | +1 | 1.6 | −2 | −2 | −2 | −2 | −2 | −2.0 |

Evaluation standards:
−2: Soft and sticky
−1: Slightly soft
0: Smooth and good spreading
+1: Slightly hard and bad spreading
+2: Hard and difficult to color

What is claimed is:
1. In a pencil-shaped stick cosmetic, the improvement which comprises adding to such cosmetic from about 0.1% by weight to about 10% by weight of

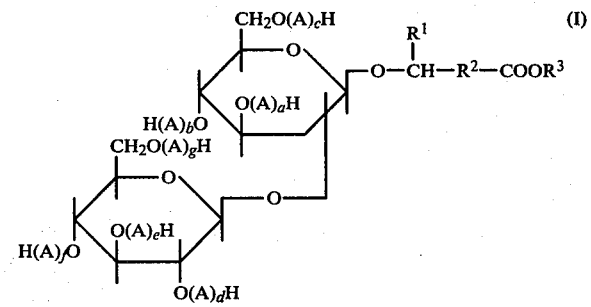

wherein $R^1$ represents a methyl group or a hydrogen atom, $R^2$ represents a saturated or unsaturated hydrocarbon group having carbon atoms of 11 to 15 when $R^1$ is a methyl group, or $R^2$ represents a saturated or unsaturated hydrocarbon group having carbon atoms of 12 to 16 when $R^1$ is a hydrogen atom, A represents the group

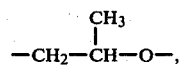

$R^3$ represents a saturated or unsaturated hydrocarbon group having carbon atoms of 1 to 20 or $-(A)_hH$, and a, b, c, d, e, f, g and h are integers, whose sums range from 1 to 60.

2. An improved stick-shaped cosmetic according to claim 1, wherein the cosmetic contains from about 0.5% by weight to about 8% by weight of the hydroxypropyl-etherified glycolipid ester.

3. The pencil-shaped stick cosmetic pencil of claim 1, wherein the cosmetic is selected from the group consisting of pencil-shaped lip rouge, pencil-shaped lip cream and pencil-shaped eye shadow.

* * * * *